United States Patent
Schall et al.

(10) Patent No.: US 9,314,291 B2
(45) Date of Patent: Apr. 19, 2016

(54) RF SURGICAL GENERATOR AND METHOD FOR DRIVING AN RF SURGICAL GENERATOR

(75) Inventors: Heiko Schall, Nuertingen (DE); Martin Fritz, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 991 days.

(21) Appl. No.: 13/266,896

(22) PCT Filed: Apr. 7, 2010

(86) PCT No.: PCT/EP2010/002186
§ 371 (c)(1),
(2), (4) Date: Nov. 17, 2011

(87) PCT Pub. No.: WO2010/124785
PCT Pub. Date: Nov. 4, 2010

(65) Prior Publication Data
US 2012/0053578 A1    Mar. 1, 2012

(30) Foreign Application Priority Data
Apr. 29, 2009 (DE) .......................... 10 2009 019 373
Aug. 17, 2009 (DE) .......................... 10 2009 037 693

(51) Int. Cl.
*A61B 18/18*    (2006.01)
*A61B 18/12*    (2006.01)

(52) U.S. Cl.
CPC .................................. *A61B 18/1206* (2013.01)

(58) Field of Classification Search
CPC ................................................. A61B 18/1206
USPC ............................................................ 606/33
See application file for complete search history.

(56) References Cited

U.S. PATENT DOCUMENTS

| | | | |
|---|---|---|---|
| 4,281,373 A | | 7/1981 | Mabille |
| 5,836,943 A | * | 11/1998 | Miller, III ........................ 606/34 |
| 6,261,286 B1 | | 7/2001 | Goble et al. |

FOREIGN PATENT DOCUMENTS

| | | |
|---|---|---|
| DE | 100 46 592 A1 | 4/2002 |
| JP | 2004-304962 A | 10/2004 |
| WO | WO 98/07378 A1 | 2/1998 |
| WO | WO 98/27880 A1 | 7/1998 |
| WO | WO 03/090635 A1 | 11/2003 |

* cited by examiner

*Primary Examiner* — Mark W Bockelman
(74) *Attorney, Agent, or Firm* — Blank Rome LLP

(57) ABSTRACT

Until now, ohmic consumers have been used to abruptly complete the output signal in RF surgical generators. Considering an RF surgical generator comprising a power supply with at least one storage capacitor and a controllable switching device with at least one energy storage device (e.g., a transformer) by which an RF output signal that can be delivered to an RF surgical instrument is generated, it is suggested herein that a regenerative device be provided between the energy storage device and the storage capacitor. Furthermore, a control mechanism is used for controlling the switching device and the regenerative device such that, if the RF output signal is to be completed, the regenerative device is energized for at least part of the time, and the energy storage is at least partially discharged in the storage capacitor.

19 Claims, 3 Drawing Sheets

RF SURGICAL GENERATOR AND METHOD FOR DRIVING AN RF SURGICAL GENERATOR

FIELD OF THE INVENTION

Embodiments of the invention relate to an RF (radio frequency) surgical generator as well as a method for driving such a generator.

BACKGROUND

Increasingly, RF surgical generators are used for tissue cutting and coagulating. Compared with mechanical incisions, haemostasis of the cutting edges is considered one of the advantages of RF surgical incisions, this haemostasis being due to thermal coagulation, in particular. In this case, the depth of the coagulation zone is largely dependent on the perfusion of the treated tissue, resulting in the requirement that the depth of the coagulation zone used by the RF surgical generators can be adjusted in as reproducible a manner as possible. In conjunction with this, the shape of the RF output signals of the RF surgical generator is of importance and, in particular, the ratio of peak value to effective value. Consequently, amplitude-modified RF voltages (currents) are selected, where the modulation is sufficient for the RF surgical generator to potentially also generate only a single cycle followed by a longer pause.

Another requirement is that the RF surgical generator be as highly efficient as possible because, if the efficiency is too low, any heat loss must be removed by elaborate cooling measures, which is not desirable in the operating room.

German Publication DE 102 18 895 A1 discloses an RF surgical generator to achieve greater efficiency in that the DC voltage power supply usually provided for such RF surgical generators can work in two modes of operation, i.e., on one hand, it can work as a power supply for the power oscillator (in a conventional manner) and, on the other hand, it can work in a mode in which an energy transfer from the power supply of the power oscillator back to the input of the DC voltage power supply takes place. In this case, substantial improvements in shaping short pulses are not possible.

German Publication DE 100 46 592 A1 discloses an RF surgical generator of the type addressed herein. In this generator, the ohmic resistance is withdrawn when the RF output signal is to be completed, said ohmic resistance being connected parallel to the consumer, as it were. The efficiency of this device, however, is minimal.

SUMMARY

An object of the embodiments of the invention is to provide an RF surgical generator of the aforementioned type, as well as a method for driving such a generator such that great efficiency and an exact and rapid shaping of the RF output signal can still be achieved.

This object is achieved by an RF surgical generator and method of operating said generator, wherein said RF surgical generator comprises a power supply with at least one storage capacitor, and comprising a controllable switching device with at least one energy storage, e.g., an output transformer, by which an RF output signal that can be delivered to an RF surgical instrument is generated. A regenerative device is connected between the energy storage and the storage capacitor and a control means is provided, said control means controlling the switching device and the regenerative device such that, if the RF output signal is to be completed, the regenerative device is energized for at least part of the time, and the energy storage is at least partially discharged in the storage capacitor.

Consequently, it is an essential aspect of the embodiments of the invention that the electrical, or also magnetic, energy that is stored in the usually provided dummy elements, e.g., the usually provided output transformer, is withdrawn from this energy storage, thus quickly resetting the RF output signal to zero. This energy that is delivered to the storage capacitor of the power supply is then available for a subsequent RF output signal. This increases the efficiency of the arrangement.

An improvement of signal controllability with—at the same time—minimal circuitry is given whenever a discharge device that drains residual energy from the energy storage is provided. To accomplish this, a transformation into thermal energy due to an ohmic load can also be used, ensuring that the oscillator will die out reliably. However, there remains a considerable increase of efficiency due to regeneration. Preferably, the discharge device is controlled by the control means such that the residual energy is drained following a partial discharge of the energy storage.

In a preferred embodiment, the energy storage comprises an output transformer, and the regenerative device comprises a separate winding on the output transformer. This way, it is possible to easily adjust the desired voltage conditions.

It is possible to accomplish regeneration via an electronic switch that is controlled by the control means. Alternatively, regeneration is possible via a diode line via which the energy storage is discharged upon the completion of the RF output signal.

Preferably, the storage capacitor of the RF surgical generator is arranged such that it—by the interposition of controlling elements—is able to absorb the excess energy of the output transformer.

The regenerative device comprises a DC/DC converter to perform an appropriate voltage adaptation. Said converter may be configured as a step-up chopper.

In an alternative embodiment, the regenerative device comprises a step-down chopper whose input voltage is adjusted to a constant voltage using an electronic switch. This embodiment of the circuit is particularly simple.

The method for driving an RF surgical generator comprising a power supply with at least one storage capacitor, and a controllable switching device with an output transformer, said device generating an RF output signal that can be delivered to an RF surgical instrument is characterized in that, for switching off the RF output signal, energy stored in the output transformer is delivered to the storage capacitor and stored in said storage capacitor. The advantages of this method have already been explained above. This applies, analogously, to corresponding developments of the method, which are apparent in view of the above-described circuit features.

BRIEF DESCRIPTION OF THE DRAWINGS

Hereinafter, exemplary embodiments of the invention are explained in greater detail with reference to drawings, in which.

DETAILED DESCRIPTION

In the description hereinafter, the same reference signs are used for components that are the same or that have the same function.

Figure 1:
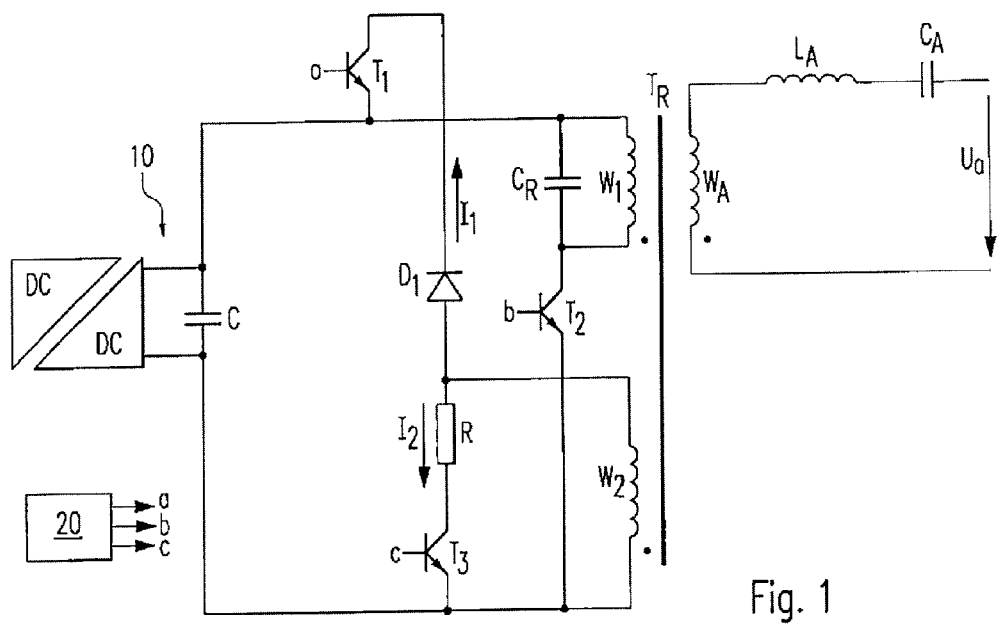
FIG. 1 is a circuit diagram of a first embodiment of the invention.

FIG. 1 shows a circuit comprising a power supply 10, where only the DC/DC converter is identified with a capacitor C located at its output. Of course, additional converter devices are provided in order to supply power to the DC/DC converter from an AC main supply.

The generator comprises an oscillating circuit $C_R$ and a (primary) winding $W_1$ of an output transformer $T_R$ and is connected to the capacitor C via transistor $T_2$. A control input "b" of transistor $T_2$ is connected to a control mechanism 20 that, consequently, can generate an oscillation due to an appropriate actuation of transistor $T_2$ in the oscillating circuit $C_R$-$W_1$, the oscillation can be delivered—via a secondary winding $W_A$ and a series oscillating circuit $L_A$, $C_A$—as the output voltage $U_a$ to an RF surgical instrument (not shown).

An additional winding $W_2$ of the transformer $T_R$ is also connected to the capacitor C via diode $D_1$ and transistor $T_1$, on one side, and via a direct line, on the other. The control input "a" of transistor $T_1$ is connected to the control mechanism 20. A series circuit comprising a resistor R and transistor $T_3$ is provided parallel to the additional winding $W_2$. A control input "c" of transistor $T_3$ is also connected to the control mechanism 20.

Figure 5:
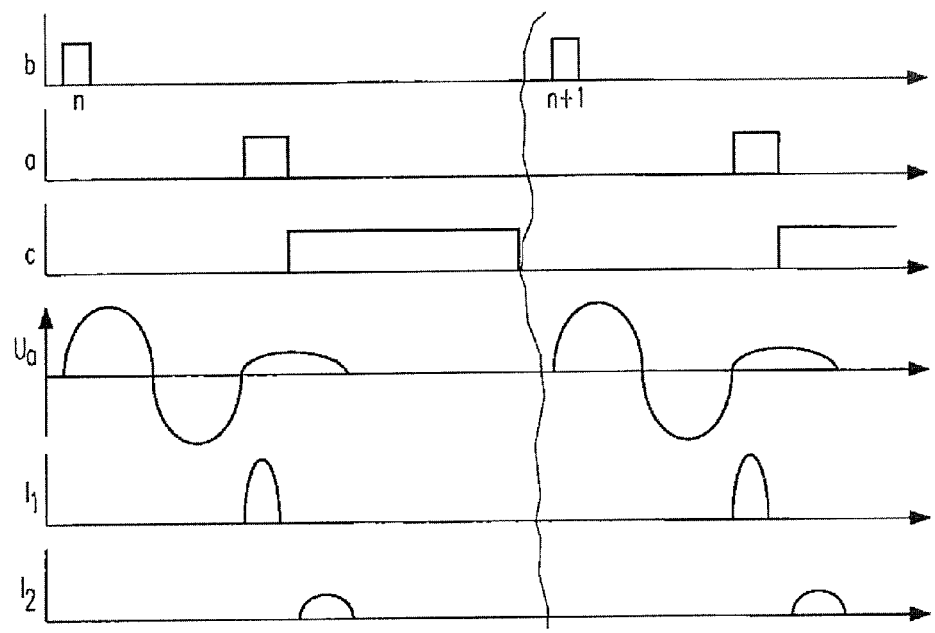
FIG. 5 is a time-dependency diagram of signal processes.

Hereinafter, the function of the circuit in accordance with FIG. 1 will be explained with reference to FIG. 5.

The control mechanism 20 generates the activation pulses n and n+1 that are delivered to the control input "b" of transistor $T_2$. By activating transistor $T_2$, the oscillating circuit $C_R$, $W_1$ is excited and generates an output voltage $U_a$.

To complete the oscillation of the oscillating circuit $C_R$, $W_1$ the control mechanism 20 generates a signal "a" that activates transistor $T_1$. As a result of this, only the additional winding $W_2$ is connected to the capacitor C via diode $D_1$ and transistor $T_1$ so that current $I_1$ flows, said current moving the energy stored in the transformer $T_R$ into the capacitor C.

Following the relatively short control pulse "a" (see FIG. 5), transistor $T_3$ is turned on by the control mechanism 20 via control input "c" of said transistor, so that only current $I_2$ flows through the resistor R, thereby converting a residual discharge of energy from the transformer $T_R$ into thermal energy. Consequently, the output voltage $U_a$ is completely set to zero; in which case a substantial quantity of the energy stored in the output transformer $T_R$ is again available on the capacitor C to be used during a subsequent activation of transistor $T_2$ via a control pulse (pulse n+1).

Figure 2:
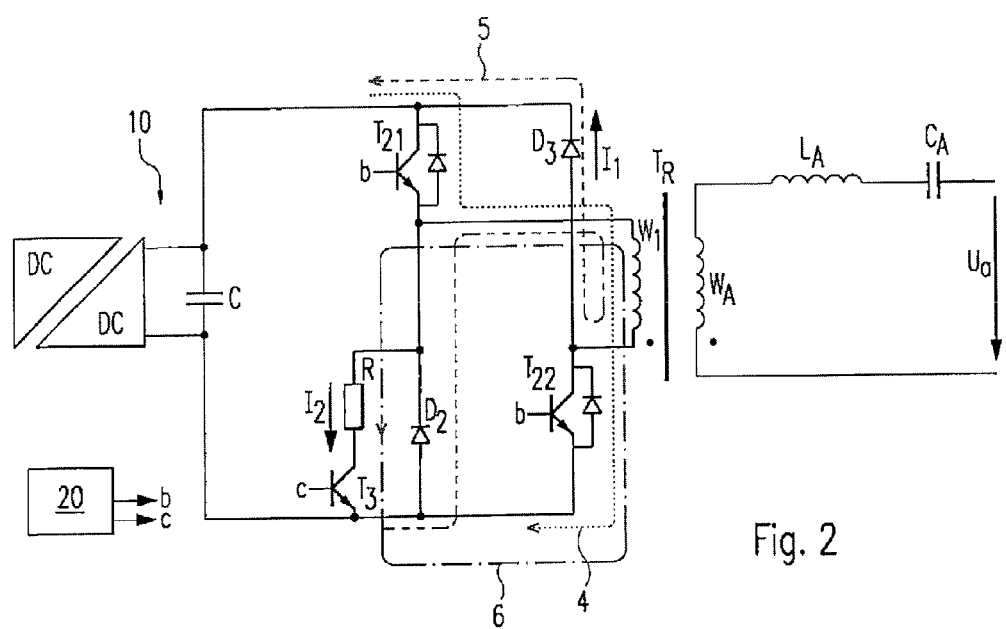
FIG. 2 is a circuit diagram of a second embodiment of the invention.

The circuit in accordance with FIG. 2 has a similar layout as the circuit in accordance with FIG. 1 considering the power supply 10 and the output circuit. Referring to this circuit, the primary winding $W_1$ of the transformer $T_R$ is connected to an upper pole of the capacitor C via transistor $T_{21}$ and to the lower pole of the capacitor C via transistor $T_{22}$. The collector/emitter lines of the two transistors $T_{21}$ and $T_{22}$ are bridged by free-wheeling diodes.

The collector of the lower transistor $T_{22}$ is connected to the upper pole of the capacitor C via diode $D_3$. The emitter of transistor $T_{21}$ is connected to the lower pole of the capacitor C via diode $D_2$, said diode $D_2$ being bridged via a series circuit comprising a resistor R and transistor $T_3$.

The current paths are indicated for explanation of the function of this circuit in accordance with FIG. 2.

When transistor $T_{21}$ and transistor $T_{2}2$ are turned on, the result is current path 4, said path 4 generating a (pulse-shaped) output voltage $U_a$. To quickly complete this output pulse (after closing transistors $T_{21}$, $T_{22}$) the energy contained as current $I_1$ in the transformer $T_R$ is returned to the capacitor C via diodes $D_2$ and $D_3$. To decrease any residual energy the control mechanism 20 activates transistor $T_3$, so that the residual energy contained as current $I_2$ in the transformer $T_R$ is converted into thermal energy via current path 6.

Figure 3:
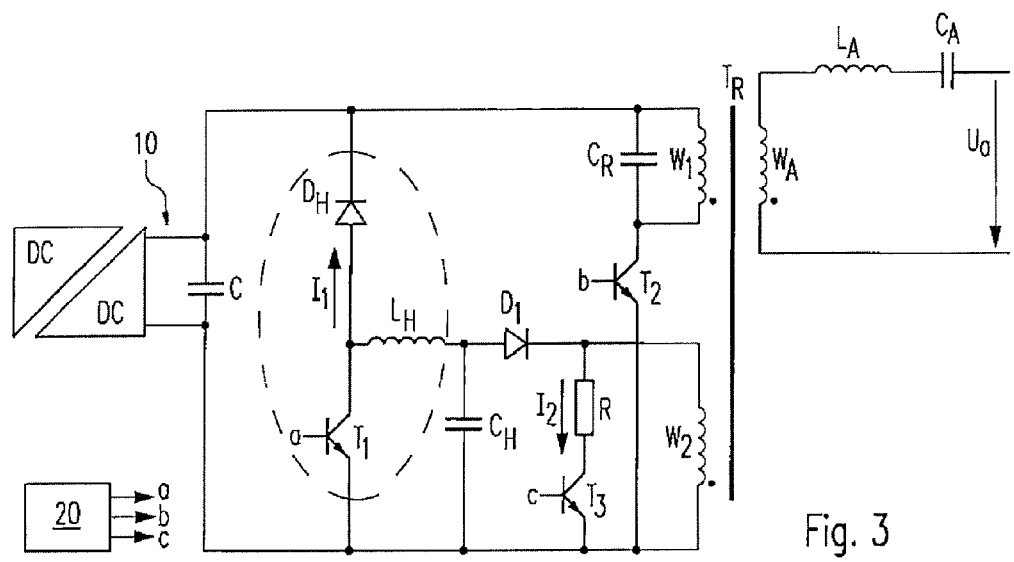
FIG. 3 is a circuit diagram of a third embodiment of the invention.

The layout shown in FIG. 3 is similar to the circuit in accordance with FIG. 1 considering the generation of oscillations and considering the transformer $T_R$. However, in this arrangement, the additional winding $W_2$ is connected to the capacitor C via a step-up chopper comprising diode $D_1$, capacitor $C_H$, inductor $L_H$ and another diode $D_H$. More precisely, a series circuit comprised of diode $D_1$ and capacitor $C_H$ is provided parallel to the additional winding $W_2$. One end of the coil $L_H$ is connected to the coupling point between the diode and the capacitor, and the other end is connected to the capacitor C via diode $D_H$. The coupling point between diode $D_H$ and inductor $L_H$ is connected to the other pole of the capacitor. C via transistor $T_1$.

Furthermore, a series circuit comprising an ohmic resistor R and a transistor $T_3$ is connected in parallel to the additional winding $W_2$.

Energization takes place in accordance with the diagram of FIG. 5; however, it is also possible to turn on the regenerative transistor $T_1$—different from the illustration of FIG. 5—as follows:

The circuit shown in FIG. 3 comprising $L_H$, $T_1$ and $D_H$ represents a step-up chopper. This step-up chopper is able to reload energy from the storage capacitor $C_H$ to the input capacitor C. Transistor $T_1$ can be turned on in pulse width modulation (PWM) mode, current regulation mode or a similar quasi-continuous mode of operation. The intent of the regulation of the step-up chopper is to maintain the voltage across the storage capacitor $C_H$ constant and, accordingly, vary the choke current by means of $L_H$.

Figure 4:
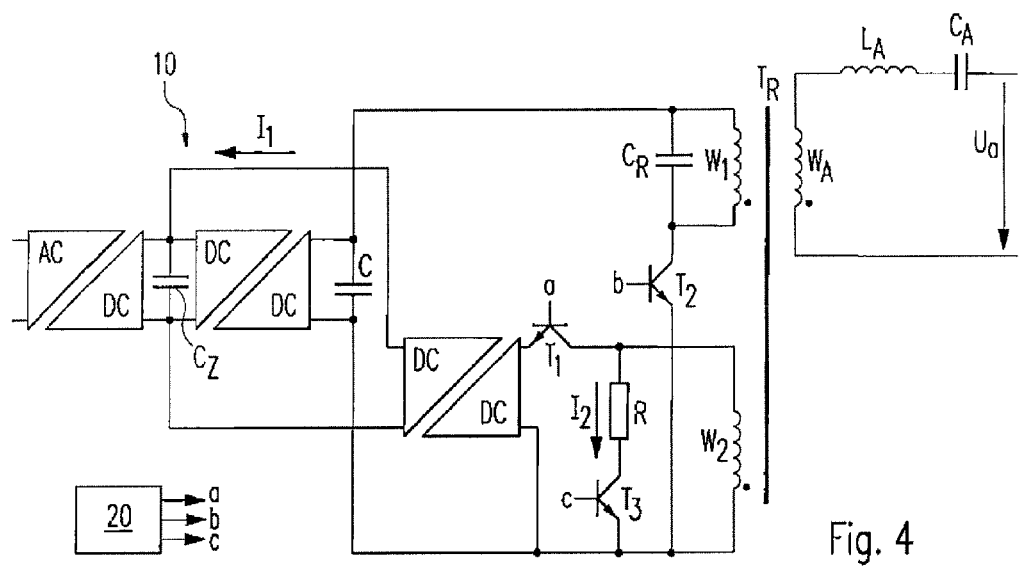
FIG. 4 is a circuit diagram of a fourth embodiment of the invention.

The circuit shown in FIG. 4 is different from that shown in FIG. 3 in that capacitor C provided in the actual generator circuit is not used, but instead capacitor $C_Z$ provided in an intermediate circuit for regenerating the energy stored in transformer $T_R$ via the current $I_1$ is used. This circuit also shows that, in the embodiment of the invention, the element that absorbs the energy stored in the output transformer $T_R$ and makes said energy available for repeated excitation and generation of an output voltage $U_A$ is not important.

Figure 6:
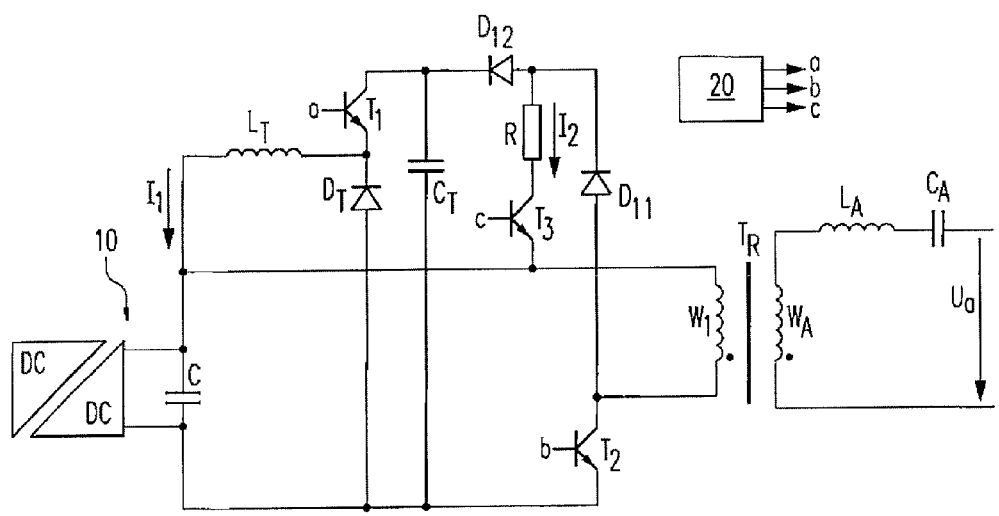
FIG. 6 is a circuit diagram of a fifth embodiment of the invention.

Considering the circuit shown in FIG. 6, again transistor $T_2$ is provided for excitation and generation of an output voltage $U_a$, said transistor $T_2$ closing an electric circuit between the output capacitor C of the power supply 10 and the primary winding $W_1$ of the transformer $T_R$ when turned on by signal "b" from the control mechanism 20.

This arrangement comprises a series circuit that is connected to the capacitor C for regenerating the energy contained in the transformer $T_R$ on the capacitor C, said circuit comprising a first diode $D_{11}$, second diode $D_{12}$, transistor $T_1$ and a coil $L_T$. The connecting point between transistor $T_1$ and the coil $L_T$ is connected to the lower pole of the capacitor C via diode $D_T$. The coupling point between diode $D_{12}$ and transistor $T_1$ is connected to the lower pole of the capacitor C via capacitor $C_T$. The connecting point between the diodes $D_{12}$ and $D_{11}$ is connected to the upper pole of the capacitor C via a series circuit comprising a resistor R and transistor $T_3$.

Considering this circuit, transistor $T_1$ is responsible for regeneration and is driven via its control input "a" by the control mechanism 20 in PWM mode (or in another controlled mode, e.g., current mode or two-point regulation) such that the input voltage of the step-down chopper set up here is regulated to a constant voltage for charging the capacitor C. Other than that, the circuit is driven like the previously driven circuits, in which case—also in this circuit (as in FIG. 2)—the generator is not a sinewave generator, but is designed for single pulse excitation. Consequently, a capacitor parallel to the primary winding $W_1$ is not necessary in this embodiment. Here, the regenerated energy is restricted to the magnetizing energy stored in the transformer.

The invention claimed is:

1. A radio frequency (RF) surgical generator comprising:
   a power supply comprising at least one storage capacitor;
   a controllable switching device comprising at least one energy storage device by which an RF output signal that can be delivered to an RF surgical instrument is generated;
   a regenerative device connected between the energy storage device and the storage capacitor; and
   a control means for controlling the switching device and the regenerative device such that, if the RF output signal is to be completed, the regenerative device is energized for at least part of the time, and the energy storage device is at least partially discharged to the storage capacitor,
   wherein the regenerative device comprises a step-down chopper whose input voltage is regulated to a constant voltage using an electronic switch.

2. The RF surgical generator of claim 1, wherein the storage device is a transformer.

3. The RF surgical generator of 1, further comprising a discharge device for draining a residual energy from the energy storage device.

4. The RF surgical generator of claim 3, wherein the discharge device comprises a conversion device for converting residual energy into thermal energy.

5. The RF surgical generator of claim 4, wherein the conversion device is an ohmic load.

6. The RF surgical generator of claim 3, wherein the discharge device is controlled by the control means such that the residual energy is drained following a partial discharge of the energy storage device.

7. The RF surgical generator of claim 1, wherein the energy storage device comprises an output transformer and the regenerative device comprises a separate winding on the output transformer.

8. The RF surgical generator of claim 1, wherein the regenerative device comprises at least one electronic switch that is controlled by the control means.

9. The RF surgical generator of claim 1, wherein the regenerative device comprises a diode path over which the energy storage device is discharged upon completion of the RF output signal.

10. The RF surgical generator of claim 1, wherein the storage capacitor is connected in series to an output transformer of the switching device.

11. The RF surgical generator of claim 1, further comprising a storage capacitor provided upstream of a DC/DC converter of the switching device.

12. The RF surgical generator of claim 1, wherein the regenerative device comprises a DC/DC converter.

13. The RF surgical generator of claim 1, wherein the regenerative device is activated in pulse width modulation mode.

14. The RF surgical generator of claim 1, wherein the regenerative device is activated in current regulation mode.

15. A method of driving an RF surgical generator comprising a power supply with at least one storage capacitor, a controllable switching device with an output transformer, and a regenerative device connected between the transformer and the storage capacitor, said method comprising:
   generating an RF output signal that can be delivered to an RF surgical instrument;
   for switching off the RF output signal, delivering energy stored in the output transformer to the storage capacitor; and
   storing the delivered energy in said storage capacitor,
   within the regenerative device, regulating the input voltage of a step-down chopper to a constant voltage using an electronic switch.

16. A radio frequency (RF) surgical generator comprising:
   a power supply comprising at least one storage capacitor;
   a controllable switching device comprising at least one energy storage device by which an RF output signal that can be delivered to an RF surgical instrument is generated;
   a regenerative device connected between the energy storage device and the storage capacitor; and
   a control means for controlling the switching device and the regenerative device such that, if the RF output signal is to be completed, the regenerative device is energized for at least part of the time, and the energy storage device is at least partially discharged to the storage capacitor,
   wherein the regenerative device comprises a step-up chopper.

17. The RF surgical generator of claim 16, wherein the regenerative device is activated in pulse width modulation mode.

18. The RF surgical generator of claim 16, wherein the regenerative device is activated in current regulation mode.

19. A method of driving an RF surgical generator comprising a power supply with at least one storage capacitor, a controllable switching device with an output transformer, and a regenerative device connected between the transformer and the storage capacitor, said method comprising:
   generating an RF output signal that can be delivered to an RF surgical instrument;
   for switching off the RF output signal, delivering energy stored in the output transformer to the storage capacitor;
   storing the delivered energy in said storage capacitor; and
   within the regenerative device, using a step-up chopper to maintain a constant voltage across the storage capacitor and to reload energy from the storage capacitor to an input capacitor.

* * * * *